United States Patent [19]

Lindner et al.

[11] Patent Number: 4,871,850
[45] Date of Patent: Oct. 3, 1989

[54] NEW TRIAZOLOPYRIMIDINES AND THEIR USE AS INITIATORS

[75] Inventors: Christian Lindner, Cologne; Dickoré Karlfried, Leverkusen; Carlhans Süling; Siegfried Korte, both of Odenthal; Wolfgang Podszun, Cologne, all of Fed. Rep. of Germany

[73] Assignee: Bayer Aktiengesellschaft, Leverkusen, Fed. Rep. of Germany

[21] Appl. No.: 141,875

[22] Filed: Jan. 6, 1988

[30] Foreign Application Priority Data

Jan. 16, 1987 [DE] Fed. Rep. of Germany ....... 3701065
Jan. 28, 1987 [DE] Fed. Rep. of Germany ....... 3702392

[51] Int. Cl.$^4$ ............ C07D 487/04; C08F 4/00
[52] U.S. Cl. .................................. 544/256; 544/281
[58] Field of Search ............... 544/281, 256; 526/204

[56] References Cited

PUBLICATIONS

Miyamoto, Y. "Synthesis of (1,2,4)Triazolo(1,5-c)-pyrimidine Derivatives", *Chem. Pharm. Bull.*, 33(7)2678-2687(1985).
Yamazaki, C., "Cyclization of Isothiosemicarbazones. IV Synthesis of the (1,2,4)Triazolo(1,5-c)pyrimidine Ring System.," *Bulletin of the Chemical Society of Japan*, vol. 54, No. 5, 1981.
March, J., *Advanced Organic Chemistry: Reactions, Mechanisms, and Structure*, p. 502 1968.
Ham, *Vinyl Polymerization*, pp. 209-210, 1967.
*Bulletin of the Chemical Society of Japan*, Band 54, 1981, C. Yamazaki; "Cyclization of Isothiosemicarbazones. IV Synthesis of the [1,2,4]triazolo-[1,5-c]-pyrimidine Ring System", Seiten 1767-1772.
*The Journal of Organic Chemistry*, Ban 50, 1985; C. Yamazaki; "Cyclization of Isothiosemicarbazones. 5. [1,2,4]-Triazolo[1,5-c]pyrimidines"; Seiten 3956-3959.
*The Journal of Organic Chemistry*, C. Yamazaki et al; "Cyclization of Isothiosemicarbazones. 6. The Formation and Structures of N-Alkenyl-1,2,4-triazoles and Related Compounds", Seiten 5513-5516.
*Chemical Abstracts*, Band 105, Nr. 11, 15. Sep. 1986; Y. Miyamoto; Yoshio: "Synthesis of [1,2,4]triazolo[1,5-c]-pyrimidine derivatives" Seite 360, Spalte 2, Zusammenfassung Nr. 97 409n.

Primary Examiner—Mukund J. Shah
Assistant Examiner—C. L. Cseh
Attorney, Agent, or Firm—Sprung Horn Kramer & Woods

[57] ABSTRACT

Triazolopyrimidines of the formula I

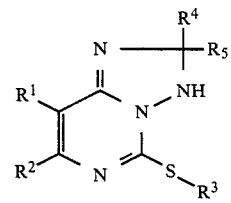

in which
$R^1$ denotes CN, alkylsulphonyl, arylsulphonyl or aryl
$R^2$ denotes H, alkyl or alkythio,
$R^3$ denotes alkyl, aralkyl, substituted aralkyl, alkenyl or alkynyl,
$R^4$ denotes alkyl, aralkyl or aryl, and
$R^5$ denotes alkyl, aralkyl or aryl, or
$R^4$ and $R^5$, together with the carbon atom, denote a carbocyclic 5-, 6- or 7-membered ring which may be substituted or bridged, in which $R^4$ cannot be methyl or aryl when $R^1$ represents CN, $R^2$ represents H, $R^3$ represents methyl and $R^5$ represents methyl or aryl, and in which alkyl preferably has 1-9 C atoms and aryl preferably has 6-12 C atoms, and also a process for their preparation, and their use as initiators.

4 Claims, No Drawings

NEW TRIAZOLOPYRIMIDINES AND THEIR USE AS INITIATORS

The invention relates to new triazolopyrimidines of the formula I

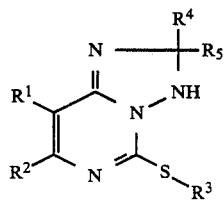

in which
- $R^1$ denotes CN, alkylsulphonyl, arylsulphonyl or aryl,
- $R^2$ denotes H, alkyl or alkylthio,
- $R^3$ denotes alkyl, aralkyl, substituted aralkyl, alkenyl or alkylnyl,
- $R^4$ denotes alkyl, aralkyl or aryl, and
- $R^5$ denotes alkyl, aralkyl or aryl, or
- $R^4$ and $R^5$, together with a carbon atom, denotes a carbocyclic 5-, 6- or 7-membered ring which may be substituted or bridged, in which $R^4$ cannot be methyl or aryl when $R^1$ represents CN, $R^2$ represents H, $R^3$ represents methyl and $R^5$ represents methyl or aryl, and in which alkyl preferably has 1–9 C atoms and aryl preferably has 6–12 C atoms.

The invention further relates to a process for the preparation of these compounds, and the use of the latter as initiators for free-radical polymerization.

Free-radical polymerization of $\alpha,\beta$-unsaturated compounds is a widespread method for the preparation of a very wide variety of polymers. Such polymerizations are conventionally catalyzed by so-called initiators, where the following may be mentioned as examples of such initiators: peroxides, azo compounds, peresters, hydroperoxides, persulphates and perphosphates. As is known, initiation by such compounds can also take place by the redox variant; in this, a redox pair of at least two compounds forms an active initiation system.

However, the activity of most initiators can be influenced by the oxygen concentration at the location of polymerization (reactor etc.). In order to reduce this influence, the polymerization is frequently carried out under nitrogen or the oxygen is compensated for by a certain, specific overdosing of initiator. The influence of oxygen in industrial polymerization is frequently difficult to verify, in particular in an enlargement of the polymerization batches. However, uniform, reproducible initiation is necessary in order to prepare high-quality polymers having uniform physical properties.

As initiators for free-radical polymerization, the compounds of the formula I are insensitive to oxygen.

The invention thus relates to the use of triazolopyrimidines of the formula (I)

I in which
- $R^1$ denotes CN, alkylsulphonyl, arylsulphonyl or aryl,
- $R^2$ denotes H, alkyl or alkylthio
- $R^3$ denotes alkyl, aralkyl, substituted aralkyl, alkenyl or alkinyl
- $R^4$ denotes alkyl, aralkyl or aryl, and
- $R^5$ denotes alkyl, aralkyl or aryl or
- $R^4$ and $R^5$, together with the carbon atom, denote a carbocyclic 5-, 6- or 7-membered ring which may be substituted or bridged, as radical initiators for the preparation of polymers based on polymerizable $\alpha,\beta$-unsaturated compounds.

The compounds of the formula (I) are 2,3-dihydro[1,2,4]triazolo[1,5-c]pyrimidines;

I

Particularly preferred compounds are those where
- $R^1$ = CN or alkylsulphonyl,
- $R^2$ = H or alkyl, in particular $C_{1-8}$-alkyl,
- $R^3$ = $C_{1-8}$-alkyl, $C_{7-13}$-aralkyl or alkenyl, in particular propenyl or allyl,
- $R^4$ = $C_1$-$C_9$-alkyl, and
- $R^5$ = $C_{1-9}$-alkyl, and $R^4$ and $R^5$ together may be $(CH_2)_n$, where $n=4$ or 5.

The compounds of the formula I can be prepared by reacting an acrylonitrile of the formula II

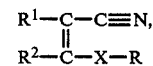

in which
$R^1$ and $R^2$ have the abovementioned meanings and R represents H or alkyl and X represents O or S, with an isothiosemicarbozone of the formula III

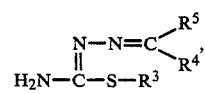

in which
$R^3$, $R^4$ and $R^5$ have the abovementioned meanings, if appropriate in the presence of a diluent.

The following 2,3-dihydro[1,2,4]triazolo[1,5-c]pyrimidines I may be mentioned individually:

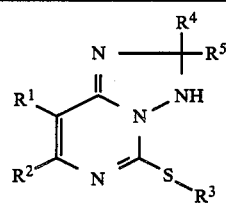

| Comp. no. | $R^1$ | $R^2$ | $R^3$ | $R^4$ | $R^5$ | m.p. (°C.) |
|---|---|---|---|---|---|---|
| I. 1 | NC | H | $CH_3$ | $CH_3$ | $CH_3$ | 176-179 (d) |
| 2 | NC | $CH_3S$ | $CH_3$ | | $-(CH_2)_5-$ | 179-186 (d) |
| 3 | NC | H | $CH_3$ | | $-(CH_2)_4-$ | 163-168 (d) |
| 4 | NC | H | $CH_3$ | | $-(CH_2)_5-$ | 192-198 (d) |
| 5 | $CH_3SO_2$ | H | $CH_3$ | | $-(CH_2)_4-$ | 140-143 (d) |
| 6 | NC | H | $CH_3$ | $CH_3$ | $C(CH_3)_3$ | 185-186 (d) |
| 7 | NC | H | $CH_3$ | $CH_3$ | $CH_2-CH(CH_3)_2$ | 128-130 (d) |
| 8 | NC | H | $CH_3$ | $CH_3$ | $CH_2-C_6H_5$ | 184-186 (d) |
| 9 | NC | H | $CH_2-C_6H_5$ | $CH_3$ | $CH_2-CH(CH_3)_2$ | 107-109 (d) |
| 10 | NC | H | $CH_2-C_6H_5$ | $CH_3$ | $C(CH_3)_3$ | 124-127 (d) |
| 11 | NC | H | $CH_2-C_6H_5$ | $CH_3$ | $C_6H_5$ | 121-126 (d) |
| 12 | NC | H | $C_2H_5$ | | $-(CH_2)_4-$ | 134-138 |
| 13 | NC | H | $CH_2-C_6H_5$ | | $-(CH_2)_4-$ | 91-93 (d) |
| 14 | NC | H | $C_2H_5$ | | $-(CH_2)_5-$ | 162-168 (d) |
| 15 | NC | H | $CH_3$ | | $-CH(CH_3)-(CH_2)_4-$ | 165-170 |
| 16 | NC | H | $CH_2-CH=CH_2$ | | $-CH(CH_3)-(CH_2)_4-$ | 122-127 (d) |
| 17 | NC | H | $CH_2-C_6H_5$ | | $-(CH(CH_3)-(CH_2)_4-$ | 135-138 (d) |
| 18 | NC | H | $CH_3$ | | $-CH_2-C(CH_3)_2-CH(CH_3)-CH_2$ | 129-132 (d) |
| 19 | NC | H | $CH_3$ | | $-C_6H_4(o)-(CH_2)_3-$ | 218 (d) |
| 20 | NC | H | $CH_2-CH=CH_2$ | | $-C_6H_4(o)-(CH_2)_3-$ | 150-152 |
| 21 | NC | H | $CH_2-C_6H_5$ | | $-C_6H_4(o)-(CH_2)_3-$ | 168-170 |
| 22 | NC | H | $CH_3$ | | $-C_6H_4(o)-(o)C_6H_4-$ | 229-232 (d) |
| 23 | NC | $CH_3$ | $CH_3$ | $CH_3$ | $CH_3$ | 172-176 (d) |
| 24 | NC | $CH_3S$ | $CH_3$ | $CH_3$ | $CH_3$ | 185-187 (d) |
| 25 | NC | $CH_3S$ | $CH_3$ | | $-(CH_2)_4-$ | 140-144 (d) |
| 26 | $C_6H_5$ | H | $C_2H_5$ | $CH_3$ | $CH_3$ | 155-158 |
| 27 | $CH_3SO_2$ | H | $CH_3$ | $CH_3$ | $CH_3$ | 173-175 (d) |
| 28 | $(CH_3)_3C-CH_2-SO_2$ | H | $CH_3$ | $CH_3$ | $CH_3$ | 160-163 (d) |
| 29 | $(CH_3)_3C-CH_2-SO_2$ | H | $C_2H_5$ | $CH_3$ | $CH_3$ | 159-160 (d) |
| 30 | $(CH_3)_3C-CH_2-SO_2$ | H | $CH_3$ | | $-(CH_2)_4-$ | 122-124 (d) |
| 31 | $(CH_3)_3C-CH_2-SO_2$ | H | $CH_3$ | $CH_3$ | $C(CH_3)_3$ | 152-156 (d) |
| 32 | $(CH_3)_3C-C_6H_4(p)SO_2$ | H | $CH_3$ | $CH_3$ | $CH_3$ | 189-190 (d) |
| 33 | $(CH_3)_3C-C_6H_4(p)SO_2$ | H | $C_2H_5$ | $CH_3$ | $CH_3$ | 155-157 (d) |
| 34 | $(CH_3)_3C-C_6H_4(p)SO_2$ | H | $C_2H_5$ | | $-(CH_2)_4-$ | 161-162 (d) |
| 35 | NC | H | $C_2H_5$ | $CH_3$ | $CH_3$ | 167-170 (d) |

Compound I.1 is known [C. Yamazaki, Bull. Chem. Soc. Jpn. 54, 1767-1772 (1981)]. The other compounds I.2 to I.35 were hitherto not known. Possible uses for such 2,3-dihydro[1,2,4]triazolo[1,5-c]pyrimidines have not previously been described.

Some of the starting materials of the formula II are known. The new compounds, for example 1-sulphonyl-acrylonitriles, can be prepared by reacting mercaptans or thiophenols IV with chloroacetonitrile to form alkyl or aryl cyanomethyl thioethers V, oxidizing them to form the corresponding sulphones VI, and preparing the acrylonitrile IIa by reaction with orthoesters.

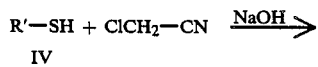

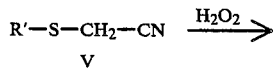

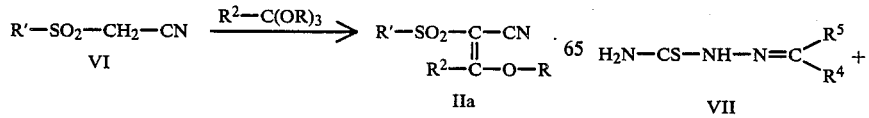

R'=alkyl or aryl.

The following acrylonitriles of the formula II, for example, can be employed:

| $R^1$ | $R^2$ | X | R | m.p.(°C.) [b.p.(°C.)/mbar] |
|---|---|---|---|---|
| NC | H | O | $C_2H_5$ | 65 [91/0.15] |
| NC | $CH_3S$ | S | $CH_3$ | 81-82 |
| $CH_3SO_2$ | H | O | $CH_3$ | 112-115 |
| NC | $CH_3$ | O | $CH_3$ | [83/0.1] |
| $C_6H_5$ | H | O | H | 159-160 |
| $(CH_3)_3C-CH_2-SO_2$ | H | O | $CH_3$ | 79-80 |
| $(CH_3)_3C-C_6H_4(p)SO_2$ | H | O | $CH_3$ | 119-121° |

Some of the starting materials of the formula III are known. The isothiosemicarbazones III which were hitherto not known can be prepared by reacting a thiosemicarbazone VII with an alkylating agent to form the isothiosemicarbazonium salt VIII, and converting this into the free base III using alkali metal hydroxide:

-continued

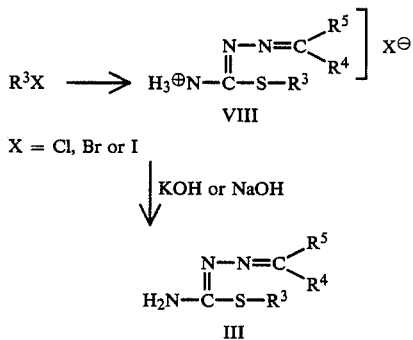

X = Cl, Br or I

The following isothiosemicarbazones of the formula III, for example, may be employed:

| $R^3$ | $R^4$ | $R^5$ | m.p. (°C.) |
|---|---|---|---|
| $CH_3$ | $CH_3$ | $CH_3$ | 59–62 |
| $C_2H_5$ | $CH_3$ | $CH_3$ | 55–56 |
| $CH_3$ | | $-(CH_2)_5-$ | 76–77 |
| $CH_3$ | | $-(CH_2)_4-$ | 61–63 |
| $CH_3$ | $CH_3$ | $C(CH_3)_3$ | 57–58 |
| $CH_3$ | $CH_3$ | $CH_2-CH(CH_3)_2$ | 28–29 |
| $CH_3$ | $CH_3$ | $CH_2-C_6H_5$ | 39–41 |
| $CH_2-C_6H_5$ | $CH_3$ | $CH_2-CH(CH_3)_2$ | Oil |
| $CH_2-C_2H_5$ | $CH_3$ | $C(CH_3)_3$ | Oil |
| $CH_2-C_6H_5$ | $CH_3$ | $C_6H_5$ | 66–68 |
| $C_2H_5$ | | $-(CH_2)_4-$ | 70–71 |
| $CH_2-C_6H_5$ | | $-(CH_2)_4-$ | 70–71 |
| $C_2H_5$ | | $-(CH_2)_5-$ | 61–63 |
| $CH_3$ | | $-CH(CH_3)-(CH_2)_4-$ | 96–97 |
| $CH_2-CH=CH_2$ | | $-CH(CH_3)-(CH_2)_4-$ | Oil |
| $CH_2-C_6H_5$ | | $-CH(CH_3)-(CH_2)_4-$ | Oil |
| $CH_3$ | | $-CH_2-C(CH_3)_2-CH_2-CH(CH_3)-CH_2-$ | 71–72 |
| $CH_3$ | | $-C_6H_4(o)-(CH_2)_3-$ | 58–59 |
| $CH_2-CH=CH_2$ | | $-C_6H_4(o)-(CH_2)_3-$ | 58–60 |
| $CH_2-C_6H_5$ | | $-C_6H_4(o)-(CH_2)_3-$ | 53–55 |
| $CH_3$ | | $-C_6H_4(o)-(o)C_6H_4-$ | 84–87 |

The compounds I are suitable for free-radical homopolymerization or copolymerization of mixtures of at least two monomers of the $\alpha,\beta$-unsaturated compound type.

Such polymerizations can be carried out in solid-phase, solution, emulsion, suspension, dispersion or precipitation polymerization.

Suitable monomers are compounds which undergo free-radical polymerization, preferably of the formula (II)

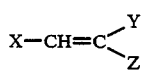

where
X=H, $C_{1-4}$-alkyl or $-CH=CH_2$, or, together with Z, form a ring, in particular X=H,
Y=H, $C_{1-4}$-alkyl, aryl, COOX (where X=H or $C_{1-4}$-alkyl), CONHX (where X=H, $C_{1-4}$-alkyl), halogen, or $-C\equiv N$,
Z=$C_{6-8}$-aryl, $C_{1-14}$-alkyl, substituted aryl, halogen, $C\equiv N$, COOX or CONX'X'',
where X' and X''=H, alkyl or aryl, where the alkyl and aryl radicals may optionally be substituted.

Preferred compounds are vinyl, allyl or maleic acid monomers. In particular styrene, α-methylstyrene, p-methylstyrene, vinyl carbonate naphthalene, acrylonitrile, methacrylonitrile, (meth)-acrylamides, (meth)-acrylic acid ethers, vinyl chloride and fluoride, vinylidene halides, maleic anhydride, maleimides, vinyl esters of $C_{1-5}$-carboxylic acids, vinyl ethers, butadiene, isoprene, chloroprene, cyclic vinyl compounds having amide structures, ethylene, propylene, butene and monomers having polyhalogenated side chains.

The initiators can be employed at temperatures from 25°–150° C., preferably in the range from 40°–100° C. At the same time, initiator concentrations from 0.01–3, preferably from 0.05–1.5% by weight, relative to 100 parts of compound to be polymerized, are preferably used.

The compounds (I) are conventionally used in similar fashion to known initiators, i.e., in the most favourable case, polymerization temperatures are used at which the initiator has a marked initiating action. These temperatures are frequently established by observing the half-value times.

The compounds (I) initiate polymerization surprisingly well in the presence of atmospheric air; initiation of a polymerization here is insensitive to variations in the air concentration, i.e. initiation delays, reduced polymer yield and uncontrolled polymer molecular weights do not arise.

The polymers obtained have good properties and high thermostabilities.

EXAMPLE 1

I. Compounds of the formula I (as initiators)

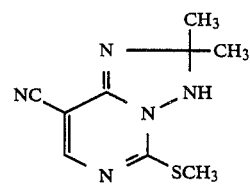

I.1

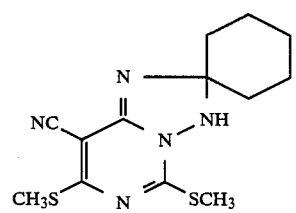

I.2

-continued

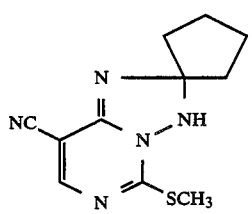
I.3

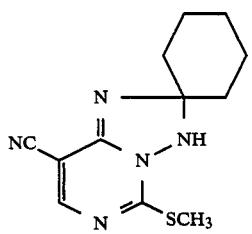
I.4

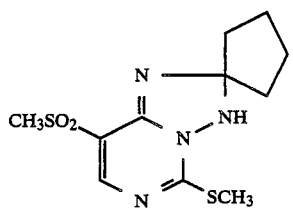
I.5

For comparison (as initiator)
I.6 cumene hydroperoxide

II. Preparation of the compounds I.1 to I.5

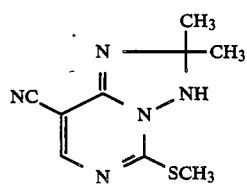
I.1

A solution of 70.8 g of ethoxymethylene-malodinitrile (0.58 mol) and 87.0 g of acetone S-methylisothiosemicarbazone (0.6 mol) in 1 liter of toluene is refluxed for 4 hours. After filtration, the product is allowed to crystallize at 0° C., and 88.0 g (68.7% of theory) of yellow crystals, which melt at 176°–179° C. with decomposition, are obtained.

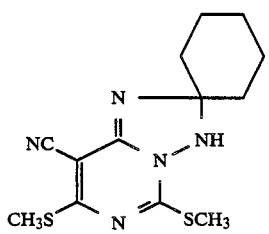
I.2

A mixture of 68.0 g of 1,1-dicyano-2,2-dimethylmercaptoethylene (0.4 mol) and 74 g of cyclohexanone S-methyl-isothiosemicarbazone is stirred with heating without solvent. From 57° C., a homogeneous melt is produced which gradually solidifies again from 89° C. The mixture is allowed to react to completion without stirring at 100° C. until the methyl mercaptan evolution is complete (about 90 minutes), 250 ml of acetonitrile are added, and the mixture is cooled to 0° C. After filtering under suction and repeatedly washing with acetonitrile, 81.0 g (66.0% of theory) of yellow crystals of melting range 179°–186° C. (decomp.) are obtained.

I.3

238 g of ethoxymethylene-malodinitrile (1.95 mol) and 333.5 g of cyclopentanone S-methyl-isothiosemicarbazone (1.95 mol) are each dissolved in 1.95 liters of toluene, and the solutions are combined with stirring at 20° C. The reaction proceeds exothermically, the temperature of the solution increases to 31° C. within 1.5 hours, and the yellow reaction product then precipitates out. After 2 days, the product is filtered off under suction and washed with a little toluene and with petroleum ether. 362.2 g (75.2% of theory) of pale yellow crystals of melting point 163°–168° C. (decomp.) are obtained.

I.4

48.8 g of ethoxymethylene-malodinitrile (0.4 mol) and 74.0 g of cyclohexanone S-methyl-isothiosemicarbazone (0.4 mol) are each dissolved in 400 ml of toluene and reacted analogously to Example 1.3. 74.4 g (71.3% of theory) of luminescent yellow crystals of melting point 192°–198° C. (decomp.) are obtained.

I.5

16.1 g of 1-methylsulphonyl-2-methoxy-acrylonitrile (0.1 mol) are added to a solution of 17.1 g of cyclopentanone S-methyl-isothiosemicarbazone (0.1 mol) in 100 ml of toluene, and the mixture is heated at 70° C. until the second component dissolves. When the slightly exothermic reaction subsides, the mixture is stirred briefly at 85° C., and the reaction product is filtered off at 20° C. under suction and washed with toluene. 18.1 g (60.3% of theory) of pale yellow needles of melting point 140°–143° C. (decomp.) are obtained.

III. Carrying out the polymerization 0.1 parts by weight of the compounds I1 to I6 are added to 50 parts by weight of styrene in a reactor. The mixture is polymerized at 100° C. for 2 hours with stirring. The mixture is then cooled, and the polymer is precipitated using alcohol. The K value of the polymers is determined at 25° C. in dimethylformamide. The experiments are carried out in the presence of air.

The results are collated in table 1.

TABLE 1

| | Styrenepolymerization | | |
|---|---|---|---|
| Experiment | Polymer yield (% by wt) | K value | Initiator employed |
| III.1 | 25 | 46 | I.1 |
| III.2 | 23 | 52 | I.2 |
| III.3 | 26 | 55 | I.3 |
| III.4 | 20 | 49 | I.4 |
| III.5 | 24 | 50 | I.5 |
| III.6 | 23 | 49 | I.6 |
| III.7 | 4 | 82 | without addition of initiator |
| III.8 | 20 | 49 | I.4* |

*During the polymerization, all operations were constantly carried out in an oxygen atmosphere (gas passed into the reactor).

EXAMPLE 2

5.0 parts by weight of acrylonitrile and 0.0125 parts by weight of the compound I.4 (from Example 1) are placed in a round-bottom flask, fitted with a stirrer device, a temperature measuring instrument, a gas-inlet tube and a reflux condenser. A gentle stream of air is passed in. After adjusting the temperature to 77° C., the reaction mixture becomes turbid due to deposition of white polymer particles. 2.5 hours after commencing the polymerization, the polymer formed is purified by introducing into 100 parts by volume of methanol and is then isolated.

Yield: 1.2 parts by weight (conversion: 24%)

$\eta_{rel} = 6.88$ (measured on a 0.5% strength by weight solution in dimethylformamide)

Under comparable conditions, no polymerization is observed without addition of compound I.4.

EXAMPLE 3

5.0 parts by weight of N-phenylmaleimide (m.p. 89° C.) and 0.0125 parts by weight of the compound I.4 (from Example 1) are placed in a round-bottomed flask, equipped with a stirrer device, a temperature measuring instrument, a gas-inlet tube and a reflux condenser. A gentle stream of air is passed in. After melting the monomer and adjusting the temperature of the reaction mixture to 90° C., polymerization sets in immediately, which can be detected from deposition of a yellowish-white polymer powder. After 2.5 hours, the poly-N-phenylmaleimide formed is isolated by stirring into 100 parts by volume of methanol.

Yield: 1.4 parts by weight (conversion: 28%)

$\eta_{rel.} = 1.17$ (measured on a 0.5% strength by weight solution in dimethylformamide)

Under comparable conditions, no polymerization is observed if compound I.4 is omitted.

EXAMPLE 4

(solution polymerization)

1. Solvent methyl ethyl ketone

A mixture of 30 parts by weight of methyl methacrylate and 10 parts by weight of a perfluoroalkyl methacrylate of the formula

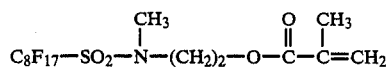

is mixed with 60 parts by weight of methyl ethyl ketone and kept at 80° C. for 4 hours after 0.4 parts by weight of the compound I.4 from Example 1 has been added as initiator to the reaction mixture.

The experiment is repeated, but without addition of the compound I.4.

The polymers resulting from the two experiments are precipitated by introducing the reaction mixture into methanol, boiling once with about 400 parts by weight of methanol and drying in a vacuum cabinet at 70° C. with compound I.4, 12.4 parts by weight of copolymer containing perfluoroalkylmethacrylate are obtained, and without compound I.4, 4.5 parts by weight of copolymer containing perfluoroalkyl methacrylate are obtained. The polymer yield which is greater by a factor of almost 3 shows the activity of the initiator according to the application.

2. Emulsion polymerization 300 parts by weight of water, 35 parts by weight of butyl methacrylate, 35 parts by weight of ethyl methacrylate, 0.35 parts by weight of the compound I.4 from Example 1 and 2.1 parts by weight of an anionic wetting agent (Hostapal BV) are emulsified in a polymerization vessel using a high-speed stirrer. The resultant dispersion is kept at 100° C. for 3 hours. A polymer dispersion having a solids content of 17.9% results. This corresponds to a conversion during the polymerization of >95%.

What is claimed is:

1. A 2,3-dihydro[1,2,4]triazolo[1,5-c]pyrimidine of the formula I

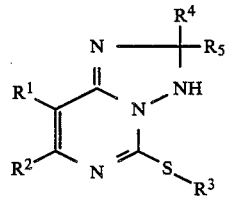

in which
R$^1$ denotes CN, C$_1$–C$_9$-alkylsulphonyl, C$_6$–C$_{12}$-arylsulphonyl or C$_6$–C$_{12}$-aryl,
R$^2$ denotes H, C$_1$–C$_9$-alkyl or C$_1$–C$_9$-alkylthio,
R$^3$ denotes C$_1$–C$_9$-alkyl, C$_7$–C$_{13}$-aralkyl, propenyl or allyl,
R$^4$ denotes C$_1$–C$_9$-alkyl, C$_7$–C$_{13}$-aralkyl or C$_6$–C$_{12}$-aryl and
R$^5$ denotes C$_1$–C$_9$ alkyl, C$_7$–C$_{12}$-aralkyl or C$_6$–C$_{12}$-aryl, or
R$^4$ and R$^5$, together with the carbon atoms which they substitute, denote a carbocyclic ring of the type selected from the group consisting of methylcyclohexane, trimethylcyclohexane, tetralene, fluorene and cyclopentane, wherein R$^4$ is not methyl or aryl when R$^1$ is CN, R$^2$ is H, R$^3$ is methyl and R$^5$ is methyl or aryl.

2. A 2,3-dihydro-[1,2,4]triazolo[1,5-c]pyrimidine according to claim 1, wherein $R^1$ denotes CN or $C_1$–$C_9$-alkylsulphonyl, $R^2$ denotes H or $C_{1-8}$-alkyl $R^3$ denotes $C_{1-8}$-alkyl, $C_{7-13}$-aralkyl, propenyl or allyl, $R^4$ denotes $C_{1-9}$-alkyl and $R^5$ denotes $C_{1-9}$-alkyl.

3. In a process for polymerizing monomers by free radical polymerization comprising reacting monomers in the presence of an initiator, the improvement comprising the initiator being a 2,3-dihydro[1,2,4]-triazolo[1,5-c]pyrimidine of the formula

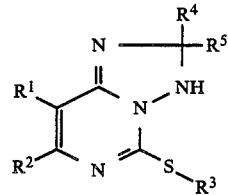

wherein
$R^1$ is CN, $C_1$–$C_4$-alkylsulphonyl, $C_6$–$C_{12}$-arylsulphonyl or $C_6$–$C_{12}$-aryl,
$R^2$ is H, $C_1$–$C_9$-alkyl, or $C_1$–$C_9$-alkylthio,
$R^3$ is $C_1$–$C_9$-alkyl, $C_7$–$C_{13}$-aralkyl, propenyl or allyl,
$R^4$ and $R^5$, independently of each other, are $C_1$–$C_9$-alkyl, $C_7$–$C_{13}$-aralkyl or $C_6$–$C_{12}$-aryl or
$R^4$ and $R^5$, together with the carbon atom which they substitute, is a carbocyclic ring of the type selected from he group consisting of methylcyclohexane, trimethylcyclohexane, tetralene, fluorane and cyclopentane.

4. A process according to claim 3, wherein the monomers are alpha, beta-unsaturated compounds.

* * * * *

UNITED STATES PATENT AND TRADEMARK OFFICE
CERTIFICATE OF CORRECTION

PATENT NO. : 4,871,850

DATED : October 3, 1989

INVENTOR(S) : Lindner et al.

It is certified that error appears in the above-identified patent and that said Letters Patent is hereby corrected as shown below:

| | |
|---|---|
| Title Page | INVENTORS: Delete " Dickore Karlfried " and substitute -- Karlfried Dickore -- |
| Title Page | ABSTRACT: 5th line delete " alkythio " and substitute -- alkylthio -- |
| Col. 4 Comp no. 18 | Under $R^5$ after " $-C(CH_3)_2-$ " add -- $CH_2-$ -- |
| Col. 5, line 41 | After "α(" delete " 62 " and substitute --β-- |

Signed and Sealed this

Twentieth Day of November, 1990

Attest:

HARRY F. MANBECK, JR.

*Attesting Officer*  *Commissioner of Patents and Trademarks*